United States Patent
Bessembinder et al.

(10) Patent No.: US 9,126,975 B2
(45) Date of Patent: *Sep. 8, 2015

(54) PROCESS FOR THE PREPARATION OF STATINS IN THE PRESENCE OF BASE

(75) Inventors: Karin Henderika Maria Bessembinder, Echt (NL); Dennis Heemskerk, Echt (NL); Ben De Lange, Echt (NL)

(73) Assignee: DSM SINOCHEM PHARMACEUTICALS NETHERLANDS B.V., Delft (NL)

( * ) Notice: Subject to any disclaimer, the term of this patent is extended or adjusted under 35 U.S.C. 154(b) by 23 days.

This patent is subject to a terminal disclaimer.

(21) Appl. No.: 13/979,976

(22) PCT Filed: Jan. 13, 2012

(86) PCT No.: PCT/EP2012/050470
§ 371 (c)(1),
(2), (4) Date: Jul. 16, 2013

(87) PCT Pub. No.: WO2012/098049
PCT Pub. Date: Jul. 26, 2012

(65) Prior Publication Data
US 2013/0296561 A1 Nov. 7, 2013

(30) Foreign Application Priority Data

Jan. 18, 2011 (EP) .................................... 11151280
Oct. 11, 2011 (EP) .................................... 11184685

(51) Int. Cl.
*C07D 405/06* (2006.01)
*C07D 413/12* (2006.01)
*C07D 419/12* (2006.01)

(52) U.S. Cl.
CPC ............ *C07D 405/06* (2013.01); *C07D 413/12* (2013.01); *C07D 419/12* (2013.01)

(58) Field of Classification Search
CPC .................................................. C07D 405/06
See application file for complete search history.

(56) References Cited

U.S. PATENT DOCUMENTS 8,524,914 B2 * 9/2013 Lee et al. .................... 548/304.7

FOREIGN PATENT DOCUMENTS

| WO | WO 9511898 | * | 5/1995 |
| WO | WO 9511898 A1 | * | 5/1995 |
| WO | WO 0049014 | * | 8/2000 |
| WO | WO 0049014 A1 | * | 8/2000 |
| WO | WO 01/96311 | | 12/2001 |
| WO | WO 02/098854 | | 12/2002 |
| WO | WO 03018555 A1 | * | 3/2003 |
| WO | WO 2005/042522 | | 5/2005 |
| WO | WO 2005042522 A1 | * | 5/2005 |
| WO | WO 2008/044243 | | 4/2008 |
| WO | WO 2010/077062 | | 7/2010 |
| WO | WO 2010/140765 | | 12/2010 |
| WO | WO 2010140765 A2 | * | 12/2010 |

OTHER PUBLICATIONS

Williams, R. "pKA Data." (c) Mar. 8, 2008. Available from: < http://research.chem.psu.edu/brpgroup/pKa_compilation.pdf >.*
International Search Report for PCT/EP2012/040470 mailed Apr. 3, 2012.
B.C. Chen et al., "Synthesis of d3-cerivastatin for use as Internal Standard in a LC/MS/MS Method Developed for Quantitation of the Drug in Human Serum", Journal of Labelled Compounds and Radiopharmaceuticals, vol. 49, 2006, pp. 311-319.
D.R. Sliskovic et al., "Inhibitors of Cholesterol Biosynthesis. 4. *trans*-6-[ 2-( Substituted-quinolinyl) ethenyl/ethyl]tetrahydro-4-hydroxy-2*H*-pyran-2-ones, a Novel Series of HMG-CoA Reductase Inhibitors", Journal of Medicinal Chemistry, 1991, vol. 34, No. 1 pp. 367-373.
Cai, Zheng-Yan et al, "*Synthesis of Hypolipidemic HMG-CoA Reductase Inhibitors*", Chinese Journal of Pharmaceuticals 2004, 35 (11), pp. 262 and 689.

* cited by examiner

*Primary Examiner* — Noble Jarrell
*Assistant Examiner* — John S Kenyon
(74) *Attorney, Agent, or Firm* — Nixon & Vanderhye P.C.

(57) ABSTRACT

The present invention relates to a process for the preparation of statins by means of a Julia-Kocienski reaction between an aldehyde and a sulfone derivative in the presence of an alkaline metal alkoxy base. The resulting derivatives are suitable as building blocks for statin type compounds such as cerivastatin, fluvastatin, pitavastatin and rosuvastatin.

6 Claims, No Drawings

PROCESS FOR THE PREPARATION OF STATINS IN THE PRESENCE OF BASE

This application is the U.S. national phase of International Application No. PCT/EP2012/050470 filed 13 Jan. 2012 which designated the U.S. and claims priority to EP 11151280.2 filed 18 Jan. 2011, and EP 11184685.3 filed 11 Oct. 2011, the entire contents of each of which are hereby incorporated by reference.

FIELD OF THE INVENTION

The present invention relates to a process for the preparation of statins by means of a Julia-Kocienski reaction between an aldehyde and a sulfone derivative in the presence of an alkaline metal alkoxy base. The resulting derivatives are suitable as building blocks for statin type compounds such as cerivastatin, fluvastatin, pitavastatin and rosuvastatin.

BACKGROUND OF THE INVENTION

Chiral diol sulfones are advanced intermediates used in preparing statins, a class of compounds useful as HMG CoA reductase inhibitors. In particular, chiral diol sulfones are employed in preparing statins in which an unsaturated carbon-carbon bond ($R_1$—CH=CH—$R_2$) is to be formed such as is the case in the antilipemic drugs cerivastatin, fluvastatin, pitavastatin and rosuvastatin.

A method for preparing chiral diol sulfones is described in WO 2002/098854 and WO 2001/096311. In these citations, a sulfone is prepared from an alcohol, more in particular tert-butyl 2-((4R,6S)-6-(hydroxymethyl)-2,2-dimethyl-1,3-dioxan-4-yl) acetate known as "Kaneka alcohol". The preparation of such an alcohol is described in EP 1024139.

Formation of unsaturated carbon-carbon bonds can be realized by the so-called Julia-Kocienski olefination (for a review see Aïssa (Eur. J. Org. Chem. 2009, 1831-1844)) between an aldehyde and the sulfones mentioned above in the presence of a base. Well-advocated bases in this respect are lithium hexamethyldisilazane (LiHMDS), potassium hexamethyldisilazane (KHMDS) and sodium hexamethyldisilazane (NaHMDS) as these bases are known for their versatility in controlling the E/Z-ratio of the products. A major drawback of these bases is that they can easily form unwanted side products which results in lower yields and difficult recovery and purification procedures.

It is an object of the present invention to provide a process wherein improved yields are obtained in comparison to the Julia-Kocienski olefination in the presence of KHMDS, LiHMDS or NaHMDS.

DETAILED DESCRIPTION OF THE INVENTION

In a first aspect of the present invention, a compound of formula (1) or the corresponding lactone form (1') can be used as starting material

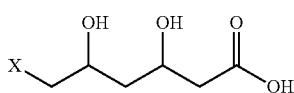
(1)

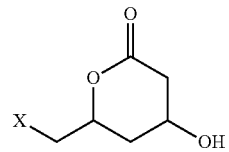
(1')

wherein X stands for halogen, like bromine or chlorine, preferably chlorine.

Prior to use in the process of the invention the hydroxyl groups and the carboxyl group of the above compounds may be protected as ketal and ester as outlined in general formula (1a) or as lactone and ether as outlined in general formula (1b)

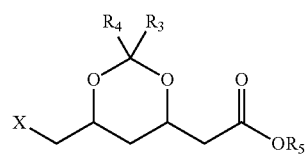
(1a)

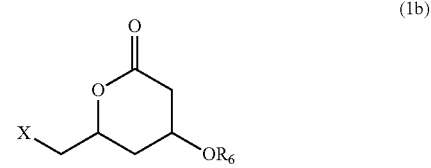
(1b)

wherein $R_3$ and $R_4$ each independently stand for an alkyl with for instance 1 to 12 C-atoms, preferably 1 to 6 C-atoms, an alkenyl with for instance 1 to 12 C-atoms, preferably 1 to 6 C-atoms, a cycloalkyl with for instance 3 to 7 C-atoms, a cycloalkenyl with for instance 3 to 7 C-atoms, an aryl with for instance 6 to 10 C-atoms or an aralkyl with for instance 7 to 12 C-atoms, each of $R_3$ and $R_4$ may be substituted and wherein $R_3$ and $R_4$ may form a ring together with the C-atom to which they are bound, use being made of a suitable acetal forming agent, in the presence of an acid catalyst, for example as described in WO 2002/06266. The groups $R_3$ and $R_4$ are for example halogens or hydrocarbon groups with for instance 1 to 10 C-atoms, optionally containing one or more heteroatoms, for instance Si, N, P, O, S, F, Cl, Br or I. In practice, $R_3=R_4$ is methyl is most preferred. In the compound of general formula (1a) $R_5$ is an alkyl or alkenyl group with one, two, three or four carbon atoms. Such relatively small substituents are generally known as being sterically unhindered or at least not very bulky. Suitable examples are allyl, iso-butenyl, n-butyl, sec-butyl, tert-butyl, ethyl, methyl, n-propyl, iso-propyl and vinyl. Preferably $R_5$ is a group that is easily introduced, small and easily removed under acidic conditions such as ethyl, methyl or iso-propyl. In the compound of general formula (1b) $R_6$ is hydrogen or an alcohol protecting group. Such a group can be any alcohol protecting group known to the skilled person such as described in, for example "Protective Groups in Organic Synthesis" (T. W. Greene, 1981, Wiley-Interscience Publication, ISBN 0-471-05764-9). These protecting groups are for example esters or ethers. These protection groups are preferred because in the final stage of conversion of these building blocks to statins, these generally acid labile or basic labile (in the case of esters) protection groups have the advantage to be removed either simultaneously with the opening of the lactone ring or by a pH shift. Hence, suitable groups $R_6$ are allyl, benzyloxymethyl, tert-butoxymethyl, tert-butyl, methoxymethyl, 1-ethoxyethyl, methoxyethoxymethyl, 4-methoxytetrahydropyranyl, methylthiomethyl, 1-(iso-propoxy)ethyl, tetrahydrofuranyl, tetrahydropyranyl, 2-methoxypropanyl, 1-propenyl, acetate, chloroacetate or benzoate. The compounds of formula (1) and (1'), and hence the compounds of formula (1a) and (1b) can be either enantiomerically pure or enriched in one of the enantiomers or racemic.

The compounds of formula (1a) or (1b) are reacted with a thiol compound of general formula $R_7$—S—X' (2) to give a compound of general formula (3a) or (3b), respectively with $R_3$, $R_4$, $R_5$ and $R_6$ as defined above.

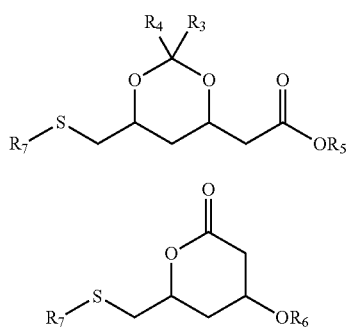

(3a)

(3b)

In the compound of general formula (2), X' represents a proton or another cation like, for example, an alkali metal ion, like sodium or potassium or lithium cation, or an ammonium ion, like tetraalkylammonium, or a phosphonium ion, like tetraalkylphosphonium. $R_7$ is an aryl group that for instance is suitable for a one-pot or modified Julia-Kocienski olefination. The Julia-Kocienski olefination is a reaction in which an aldehyde of formula $R_1$—CH=O is reacted with a sulfone of formula $R_2$—$CH_2$—$SO_2$—$R_7$ to form an olefinic bond, i.e. $R_1$—CH=CH—$R_2$. The original Julia olefination requires two steps. In the modified reaction (Julia-Kocienski olefination), the intermediate obtained in the reaction with an aldehyde undergoes spontaneous elimination to give the olefin.

Preferably, the aryl group $R_7$ is a residue sufficiently π-electron deficient to be suitable for the modified (or one-pot) Julia-Kocienski olefination. In particular, it is preferred, that the aryl group is capable to promote a so-called Smiles rearrangement. Preferably, the thiol-aryl compound contains as an aryl group an aromatic moiety having a hetero atom, more preferably nitrogen. More in particular, the aromatic residue contains an electrophilic imine-like moiety within the heterocycle. Suitable aryl groups are e.g. described in P. R. Blakemore, J. Chem. Soc., Perkin Trans. 1, 2002, 2563. Particularly suitable in this respect are substituents $R_7$ of general formula $R_{7'}$ and $R_{7''}$

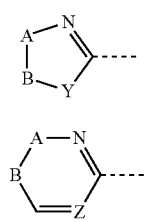

($R_{7'}$)

($R_{7''}$)

wherein A-B is C=C or N=N or wherein A-B is part of a aromatic five- or six-membered ring, wherein Y is sulfur or alkyl-substituted nitrogen, preferably tert-butyl-substituted nitrogen, ethyl-substituted nitrogen, methyl-substituted nitrogen or phenyl-substituted nitrogen and wherein Z is nitrogen or CH. Preferred aryl groups include tetrazole, substituted phenyl and benzimidazole type compounds. Specific examples of preferred aryl groups include 3,5-bis(trifluoromethyl)phenyl-1-yl, pyridine-2-yl, pyrimidin-2-yl, benzothiazol-2-yl, 1-methyl-1H-tetrazol-5-yl, 1-phenyl-1H-tetrazol-5-yl, 1-tert-butyl-1-H-tetrazol-5-yl, 1-methylimidazol-2-yl, benzimidazol-2-yl, 4-methyl-1,2,4-triazol-3-yl and iso-quinolin-1-yl. Most preferred aryl groups are 3,5-bis(trifluoromethyl)phenyl-1-yl, 1-methyl-1H-tetrazol-5-yl, 1-phenyl-1H-tetrazol-5-yl, 1-tert-butyl-1-H-tetrazol-5-yl and benzothiazol-2-yl.

The reaction from (1a) or (1b) to (3a) and (3b), respectively will take place under suitable conditions wherein it is generally important to preclude harsh conditions (like temperatures above 130° C. or exceedingly long reaction times or application of strongly basic or acidic conditions) in order to preclude degradation of the starting compound or the thiol obtained. Suitable reaction conditions are temperatures about 50° C. or higher, preferably about 80° C. or higher, and more in particular about 100° C. or higher. Generally, the temperature will be about 150° C. or lower, preferably about 140° C. or lower, and more in particular about 130° C. or lower. In case a temperature at the higher end-range is chosen, care should be taken to choose the time period such, that limited degradation occurs. Limited degradation is less than 10% of the starting halomethyl compound of general formula (1a) or (1b), preferably less than 5%, more in particular less than about 3%. Generally, a reaction time of less than about 20 h, preferably less than about 10 h should be possible in case the reaction conditions are chosen properly. However, the time period is not critical, and may be up to 30 h or longer. Generally, the reaction takes longer than about 1 h, but this is strongly dependant on the reaction conditions, reaction engineering aspects (like reactor design or application of rate-accelerating means like application of ultrasound or microwave irradiation) and amounts of reagents used, and this is not critical.

The reaction to obtain the thio-ether can be performed in a solvent or without the presence of a solvent. In case a solvent is used, the concentration of halomethyl starting compound of general formula (1a) or (1b) is generally about 10 wt % or higher, preferably about 30 wt % or higher, more in particular about 40 wt % or higher. Preferably, the reaction is carried out with a relatively high concentration of halomethyl starting compound of general formula (1a) or (1b) of 70 to 99 wt %.

Suitable solvents are dimethylsulfoxide (DMSO), N-methyl pyrrolidone (NMP), dimethylformamide (DMF), sulfolane, acetonitrile, glymes (alkyl-capped or uncapped mono-, oligo-, or poly-ethylene glycol ethers of varying chain length) or other polar non-protic solvents or alcohols like methanol, ethanol, 2-propanol, or halogenated hydrocarbons like dichloromethane, chloroform, 1,2-dichloroethane, optionally in combination with non-polar solvents like toluene or methyl tert-butyl ether (MTBE). It is also possible to use biphasic solvent systems consisting of an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). These phase transfer-catalysts are also very suitable for use in mono-phasic solvent systems. Another class of suitable solvents comprises ionic liquids like, for example, 1,3-dialkyl imidazolium salts or N-alkyl pyridinium salts of acids like hexafluorophosphoric acid or tetrafluoroboric acid or trifluoromethane sulfonic acid, or with $(CF_3SO_2)_2N^-$ as anionic counterpart.

The amounts of reagents can be chosen from a wide range. It is preferred to use a rate-enhancing excess of thiol compound, as the excess thiol that remains after reaction with the halomethyl derivative can be easily removed by washing with water at high pH. The molar amount of thiol to halogen compound generally is about 0.5 to 1 or higher, preferably 1 to 1 or higher, more preferably 1.1 to 1 or higher. Generally, the amount of thiol to halogen compound will be 3 to 1 or lower, preferably 2 to 1 or lower, most preferably 1.5 to 1 or lower. Preferably excess thiol is recovered for re-use which is easily achieved with the thiols of the present invention.

The thio-ether compound of general formula (3a) or (3b) can be isolated from the reaction mixture, or the mixture can be used as such in a subsequent oxidation reaction. Preferably, the reaction mixture is treated so as to remove excess thiol compound or excess halogen compound as the case may be. Any excess thiol compound can be easily removed by extraction with water at pH higher than 7, preferably higher than 8, more preferably of about 9 or higher. Suitable extraction agents are for example saturated caustic soda solution, saturated bicarbonate solution, or diluted sodium hydroxide solution. After extraction, the thio-ether compound of general formula (3a) or (3b) can be isolated by removal of the solvent by distillation, or by crystallization or precipitation, e.g. by addition of (or solvent switch to) an anti-solvent like hexane, heptane, iso-octane, or water. It is however not necessary to remove the solvent, as the oxidation can be performed in the same solvent. It is however preferred, to remove water from the reaction mixture, in case water interferes with the oxidation reaction. Hence, in a preferred embodiment of the invention, the oxidation is carried out without purification of the thio-ether compound of general formula (3a) or (3b), more preferably in the same solvent as was used in the etherification reaction.

For the purpose of the present invention, a halogen derivative can be used as starting compound. This is advantageous because the Kaneka alcohol generally is prepared from such a halogen derivative. Therefore, the present invention provides a process, in which additional steps in the prior art are made obsolete if the chiral diol sulfone is to be used in a Julia-Kocienski olefination.

The thio-ether compound of general formula (3a) or (3b) is oxidized in manners known in the art, for example by oxidation with hydrogen peroxide or peracids (e.g. 3-chloroperoxybenzoic acid, peroxyacetic acid, monoperoxyphthalic acid), bleach, tert-BuOCl, perborates, N-oxides, permanganate, chromate, chlorate, bromate, perchlorate, periodate, tert-butyl hydroperoxide, oxone, peroxodisulfates and air/oxygen. The oxidation can be carried out in the presence of an appropriate catalyst, such as salts or oxides of the metals V, Ce, Mn, Ni, Fe, Cu, Os, Mo, W, Re, or Ru or organic catalysts like iso-butyraldehyde in the case of air/oxygen or tetramethylpiperidine N-oxide (TEMPO) in the case of bleach. The resulting sulfones are of general formula (4a) and (4b), respectively, with $R_3$, $R_4$, $R_5$, $R_6$ and $R_7$ as defined above.

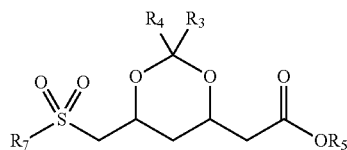

(4a)

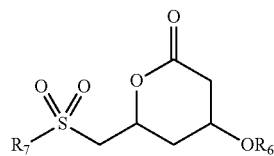

(4b)

The oxidation is performed in a solvent such as dichloromethane, chloroform, 1,2-dichloroethane, methanol, ethanol, 2-propanol, acetonitrile, acetic acid, toluene, water, NMP, DMSO, DMF, tetrahydrofuran (THF) or MTBE. Alternatively, biphasic solvent systems may be used. These may be an aqueous phase and an organic phase in the presence of a phase-transfer catalyst, like quaternary ammonium salt or quarterly phosphonium salt (like tetraalkylammonium halide, e.g. tetrabutylammonium bromide) or crown ether (like 18-crown-6). Other suitable solvents are ionic liquids like, 1,3-dialkyl imidazolium salts or N-alkyl pyridinium salts of acids like hexafluorophosphoric acid or tetrafluoroboric acid or trifluoromethane sulfonic acid or with $(CF_3SO_2)_2N^-$ as anionic counterpart. A reaction temperature of about $-20°$ C. or higher is effective.

For the oxidation, a temperature of about $0°$ C. or higher is applied, more preferably a temperature close to ambient temperature (18-25° C. i.e. around 20° C.). A temperature of about 150° C. or lower (preferably 100° C. or lower, more preferably 60° C. or lower, most preferably 40° C. or lower) usually is effective. The molar amount of oxidant to thio-ether generally is about 1 to 1 or higher, preferably about 2 to 1 or higher, more preferably about 3 to 1 or higher. Generally, the amount of oxidant to thio-ether will be about 20 to 1 or lower, preferably about 10 to 1 or lower, most preferably about 5 to 1 or lower. The sulfone of general formula (4a) or (4b) can be isolated by aqueous extraction of excess oxidant/catalyst and subsequent removal of the solvent by evaporation. If water-miscible solvents like alcohols or aprotic polar solvents are applied as reaction medium, the reaction mixture can be partitioned between an aqueous and an organic phase prior to this operation, in order to extract the solvent to the aqueous phase. If ionic liquids are applied as reaction medium, the sulfone can be isolated by extraction with an organic solvent immiscible with the ionic liquid, followed by evaporation of the solvent. Alternatively, the sulfone can be isolated from the reaction mixture by precipitation or crystallization, e.g. by addition of (or solvent switch to) an anti-solvent like hexane, heptane, iso-octane, or water. If desired, purification of the sulfone can be performed by chromatography or, preferably, by re-crystallization from (or trituration with) a suitable solvent, like 2-propanol or another solvent, depending on the aryl group used with the thiol compound of formula (2) and the residues $R_3$, $R_4$, $R_5$ and $R_6$ used with the initial halomethyl compounds of formula (1a) or (1b).

In the present invention, the sulfone of general formula (4a) or (4b) is treated with an aldehyde $R_1$—CH=O, in which $R_1$ is chosen so as to obtain suitable precursors to useful statin-type compounds including pitavastatin, rosuvastatin, fluvastatin, and cerivastatin, or in which $R_1$ is a suitable precursor to these moieties (cf. WO 2002/098854 and WO 2001/096311). Preferred examples of aldehyde $R_1$—CH=O are 4-(4-fluorophenyl)-2,6-diisopropyl-5-(methoxymethyl)nicotinaldehyde, 3-(4-fluorophenyl)-1-isopropyl-1H-indole-2-carbaldehyde, 2-cyclopropyl-4-(4-fluorophenyl)-quinoline-3-carbaldehyde and N-(4-(4-fluorophenyl)-5-formyl-6-isopropylpyrimidin-2-yl)-N-methylmethanesulfonamide as these aldehydes are the precursors for cerivastatin, fluvastatin, pitavastatin and rosuvastatin, respectively. Thus, $R_1$ preferably is a radical chosen from the list consisting of the radicals of formula (A), (B), (C) and (D):

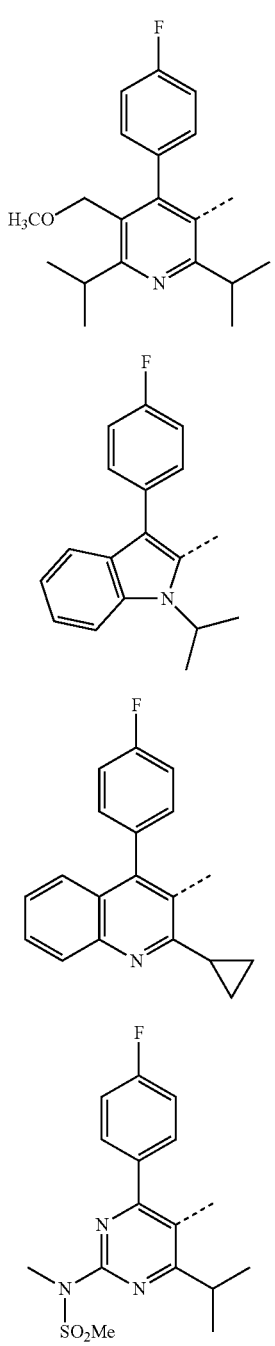

dec-7-ene (DBU) and the like. Whereas the E/Z-ratio in the final product depends on various parameters, such as type of base, thio-substituent ($R_7$) and solvents, as for instance outlined in P. R. Blakemore et al. (Synlett 1998, 26-28), this ratio normally varies between 40:60 and 80:20 in customary solvents such as diethyl ether, dimethoxyethane, tetrahydrofuran and toluene.

Surprisingly it was found that in the condensation reaction of the present invention, i.e. starting from compounds of general formula (4a) and (4b) and aldehydes $R_1$—CH=O, a marked improvement is achieved when using bases having a pKa value between 15 and 22, preferably between 16 and 21 and more preferably between 17 and 20. When using bases having a higher pKa value, such as described in the prior art (KHMDS, LiHMDS or NaHMDS) in the synthesis of rosuvastatin, wherein $R_1$ is a radical of formula (D), significant amounts of side products are found. For example, de-protonation of the methyl group a to the sulfone moiety in (D) leads to 15-20% of unwanted impurities. Surprisingly, when the bases of the present invention are used, these amounts are only 1-2%, under otherwise same conditions. Particularly suitable examples of bases in this respect are alkaline metal alkoxy bases such as lithium tert-butoxide, lithium ethoxide, lithium methoxide, potassium tert-butoxide, potassium ethoxide, potassium methoxide, sodium tert-butoxide, sodium ethoxide and sodium methoxide. These alkaline metal alkoxy bases have significant additional advantages as, compared to the prior art bases, they are less sensitive towards traces of water, can be used in solvents that are difficult to dry (like tert-butanol), are easier to handle, are less expensive and lead to smaller and less toxic waste streams as is the case with the silicon-comprising bases such as KHMDS, LiHMDS and NaHMDS.

In addition a marked difference is observed between lithium-comprising bases and sodium-comprising bases where the latter strongly favors extremely high E/Z-ratio's. This is advantageous as the E-configuration is the required configuration in cerivastatin, fluvastatin, pitavastatin and rosuvastatin. Hence, the use of a sodium-comprising base precludes laborious removal and/or recycling of undesired Z-isomer.

Following the Julia-Kocienski olefination between compounds (4a) or (4b) and aldehyde $R_1$—CH=O the resulting products (5a) and (5b), respectively may be isolated and purified after which they are deprotected to give product (6). Alternatively deprotection may be carried out without isolation and/or purification of intermediate products (5a) and (5b). Deprotection is carried out according to procedures known to the skilled person, for instance by using acid such as hydrochloric acid as described in U.S. Pat. No. 6,844,437 or WO 2007/000121.

The above Julia-Kocienski olefination between compounds (4a) or (4b) and aldehyde $R_1$—CH=O is carried out in the presence of a base, examples of which are lithium hydride, potassium hydride, sodium hydride, KHMDS, LiHMDS, NaHMDS, solid potassium hydroxide, solid sodium hydroxide, alkaline metal alkoxy bases, lithium bis-trimethylsilylamide (LiN(TMS)$_2$), sodium bis-trimethylsilylamide (NaN(TMS)$_2$), potassium bis-trimethylsilylamide (KN(TMS)$_2$), sodium amide, P4-tBu, 1,8-diazabicyclo[5.4.0]un-

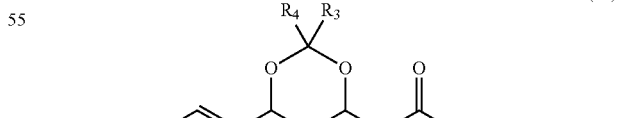

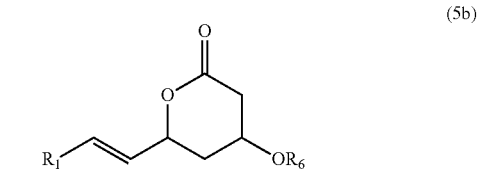

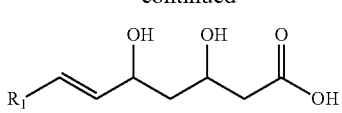
(6)

In a second aspect of the invention there is disclosed a compound of general formula (5a) wherein $R_1$ is a radical chosen from the list consisting of the radicals of formula (A), (B), (C) and (D)

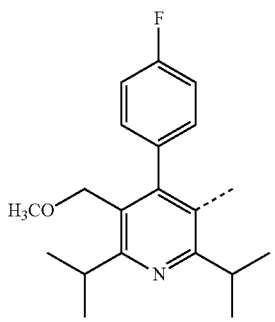
(A)

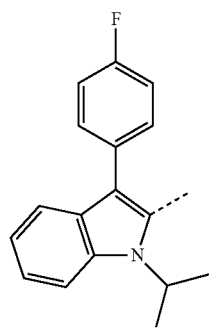
(B)

(C)

(D)

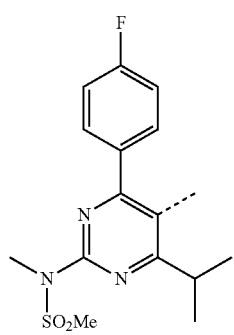

and wherein $R_3$ and $R_4$ each independently stand for an alkyl with for instance 1 to 12 C-atoms, preferably 1 to 6 C-atoms, an alkenyl with for instance 1 to 12 C-atoms, preferably 1 to 6 C-atoms, a cycloalkyl with for instance 3 to 7 C-atoms, a cycloalkenyl with for instance 3 to 7 C-atoms, an aryl with for instance 6 to 10 C-atoms or an aralkyl with for instance 7 to 12 C-atoms, each of $R_3$ and $R_4$ may be substituted and wherein $R_3$ and $R_4$ may form a ring together with the C-atom to which they are bound, use being made of a suitable acetal forming agent, in the presence of an acid catalyst, for example as described in WO 2002/06266. The groups $R_3$ and $R_4$ are for example halogens or hydrocarbon groups with for instance 1 to 10 C-atoms, optionally containing one or more heteroatoms, for instance Si, N, P, O, S, F, Cl, Br or I. Preferably $R_3=R_4$ is methyl. In the compound of general formula (1a) $R_5$ is an alkyl or alkenyl group with one, two, three, four, five or six carbon atoms. Novel and preferred examples are those wherein $R_5$ is an alkyl with four, five or six carbon atoms. It was found that, apart from compounds wherein $R_5$ is an alkyl with one, two or three carbon atoms, also the compounds with four, five or six carbon atoms are suitable from a preparative and economic point of view. Particular suitable examples in this respect are iso-butenyl, n-butyl, sec-butyl, tert-butyl, 3-methylbutan-2-yl, 4-methylpentan-2-yl and 2-pentyl.

EXAMPLES

Example 1

Preparation of 2-(4R,6S)-6-((benzo[d]thiazole-2-ylthio)methyl)-2,2-dimethyl-1,3-dioxan-4-yl)acetic acid sec-butyl ester (B) from (4R,6S)-6-(chloromethyl)-2,2-dimethyl-1,3-dioxan-4-yl)acetic acid sec-butyl ester (A) and 2-mercapto-1H-benzothiazole (2-MBT)

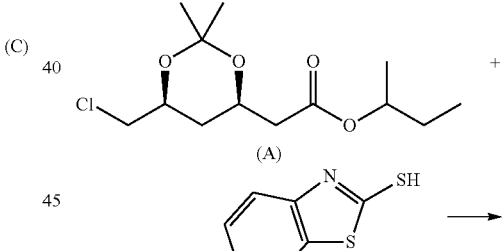
(A)

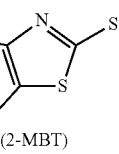
(2-MBT)

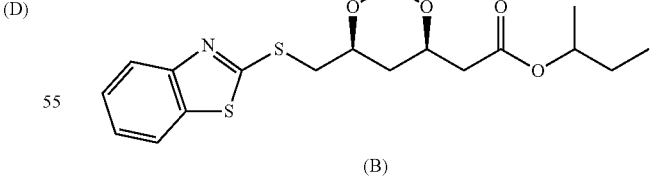
(B)

A reactor was charged with 297.5 g (1.07 mol) of compound A and 1160 mL of N-methylpyrrolidone. To this solution was added 214 g 2-MBT (1.2 eq. 1.28 mol), 117 g NaHCO$_3$ (1.3 eq., 1.39 mol) and 0.69 g tetra-n-butyl ammonium bromide (TBAB). The reaction mixture was stirred for 23 h at 90° C. and then cooled to RT, diluted with 1.5 L of methyl-tert-butyl ether and washed with 1 L of saturated aqueous NaHCO$_3$. The organic layer was washed again with 2×700 mL of saturated aqueous NaHCO$_3$ and 2×700 mL of water. The resulting brown organic layer was treated with 20 g active carbon. After removal of the carbon by filtration, the organic layer was concentrated to give 2-(4R,6S)-6-((benzo[d]thiazole-2-ylthio)methyl)-2,2-dimethyl-1,3-dioxan-4-yl) acetic acid sec-butyl ester (compound B), as a yellow oil. Yield 301.8 g (69%). $^1$H NMR (300 MHz, CDCl$_3$) δ 7.91 (d, 1H), 7.76 (d, 1H), 7.49-7.39 (m, 1H), 7.36-7.28 (m, 1H), 4.96-4.77 (m, 1H), 4.40-4.21 (m, 2H), 3.53 (add, 2H), 2.46 (ddd, 2H), 1.84 (dt, 1H), 1.65-1.49 (m, 2H), 1.46 (s, 3H), 1.39 (s, 3H), 1.36-1.22 (m, 1H), 1.20 (dd, 3H), 0.89 (m, 3H).

Example 2

Preparation of 2-((4R,6S)-6-((benzo[d]thiazol-2-ylsulfonyl)methyl)-2,2-dimethyl-1,3-dioxan-4-yl) acetic acid sec-butyl ester (C) from 2-(4R,6S)-6-((benzo[d]thiazole-2-ylthio)methyl)-2,2-dimethyl-1,3-dioxan-4-yl)acetic acid sec-butyl ester (B)

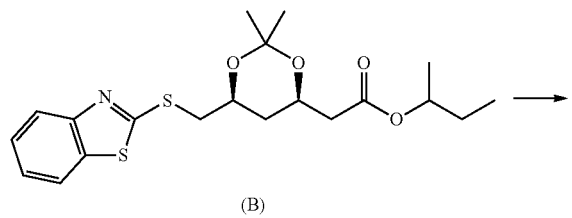

(B)

(C)

A) Procedure Using m-CPBA 2-(4R,6S)-6-((benzo[d]thiazole-2-ylthio)methyl)-2,2-dimethyl-1,3-dioxan-4-yl)acetic acid sec-butyl ester (B, 2.48 g, 6.0 mmol) and 1.9 g NaHCO$_3$ (22.8 mmol; 3.8 equiv.) were added to 50 mL of dichloromethane at 0° C. Then 4.1 g m-CPBA (16.8 mmol; 2.8 equiv) was added slowly keeping the temperature below 5° C. (slightly exothermic). When addition was completed, the temperature was allowed to raise to 20-25° C. and stirred for 18 h. The mixture was diluted with 50 mL of dichloromethane and the precipitated salts were removed by filtration. The organic layers was washed with 2×100 mL of 10 w/w % aqueous NaHSO$_3$ and 4×100 mL of 5 w/w % aqueous Na$_2$CO$_3$ After drying on Na$_2$SO$_4$, the dichloromethane was evaporated. The resulting thick oil was stirred in isopropanol to give compound 2-((4R,6S)-6-((benzo[d]thiazol-2-ylsulfonyl)methyl)-2,2-dimethyl-1,3-dioxan-4-yl)acetic acid sec-butyl ester as a white solid (C, 0.54 g, yield 20%). $^1$H NMR (300 MHz, CDCl$_3$) δ 8.22 (d, 1H), 8.01 (d, 1H), 7.70-7.51 (m, 2H), 4.85 (m, 1H), 4.59 (ddt, 1H), 4.40-4.24 (m, 1H), 3.87 (dd, 1H), 3.42 (dd, 1H), 2.45-2.35 (m, 2H), 1.71 (d, 1H), 1.43 (d, 2H), 1.36-1.33 (m, 4H), 1.18 (dd, 3H), 0.87 (dt, 3H), 0.78 (s, 3H).

B) Procedure Using Na$_2$WO$_4$.2H$_2$O and 30% H$_2$O$_2$ 2-(4R,6S)-6-((Benzo[d]thiazole-2-ylthio)methyl)-2,2-dimethyl-1,3-dioxan-4-yl)acetic acid sec-butyl ester (B, 4 g, 9.8 mmol) was dissolved in 20 mL of methanol and Na$_2$WO$_4$.2H$_2$O (0.3 g, 10 mol %) was added. Next, 3 mL of 30% H$_2$O$_2$ solution was added in 1 h at 25° C. while keeping the pH at about 8.5 using aqueous 4M NaOH. After the addition was completed, the mixture was stirred for 18 h. The precipitated solid was isolated by filtration. The solid was dissolved in ethylacetate and washed 2 times with 10 w/w % aqueous Na$_2$SO$_3$. The organic layer was evaporated and the resulting solid was re-crystallized from isopropanol to give 2-((4R,6S)-6-((benzo[d]thiazol-2-ylsulfonyl)methyl)-2,2-dimethyl-1,3-dioxan-4-yl)acetic acid sec-butyl ester as a white solid (2.46 g, yield 57%). NMR identical as given under procedure A using m-CPBA.

C) Procedure Using Na$_2$WO$_4$.2H$_2$O and 30% H$_2$O$_2$ (270 g Scale)

A reactor was filled with 270 g (0.66 mol) of compound B, 21.7 g Na$_2$WO$_4$.2H$_2$O (10 mol %) and 1940 mL of methanol. To this mixture was added in 2 h, 222 mL of a 30% H$_2$O$_2$ solution (3.3 eq.), keeping the temperature at 20° C. and the pH at 8 using aqueous 4M NaOH. When the addition was completed, the reaction mixture was stirred for 23 h. The precipitated product was filtered and washed with methanol (100 mL). To the filtrate was added water (500 mL) to precipitate more solid. The product was filtered. The combined solids were dried to give 164 g of crude product. The crude material was re-crystallized from isopropanol, to give 125 g of 2-((4R,6S)-6-((benzo[d]thiazol-2-ylsulfonyl)methyl)-2,2-dimethyl-1,3-dioxan-4-yl)acetic acid sec-butyl ester (C). The filtrate was concentrated to about 150 mL to give another 19 g of compound C. In total 144 g of compound C (yield=41%) was obtained.

Example 3

Preparation of 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl) acetate, sec-butyl ester (E) from N-(4-(4-fluorophenyl)-5-formyl-6-isopropylpyrimidin-2-yl)-N-methylmethanesulfonamide (D) and 2-((4R,6S)-6-((benzo[d]thiazol-2-ylsulfonyl)methyl)-2,2-dimethyl-1,3-dioxan-4-yl)acetate sec-butyl ester (C)

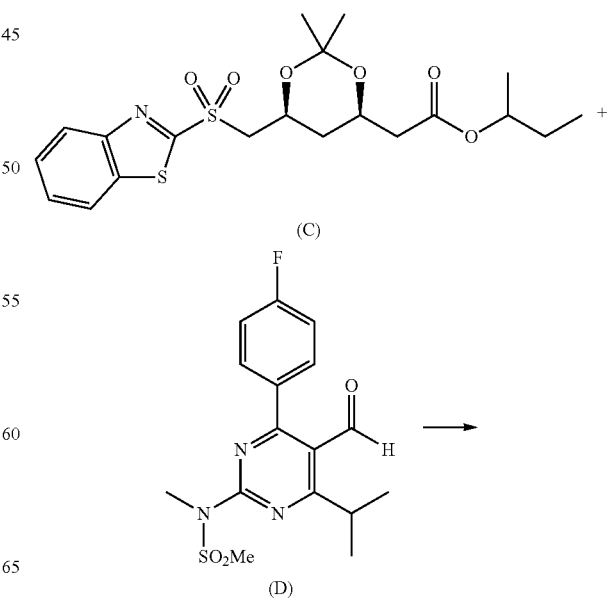

-continued

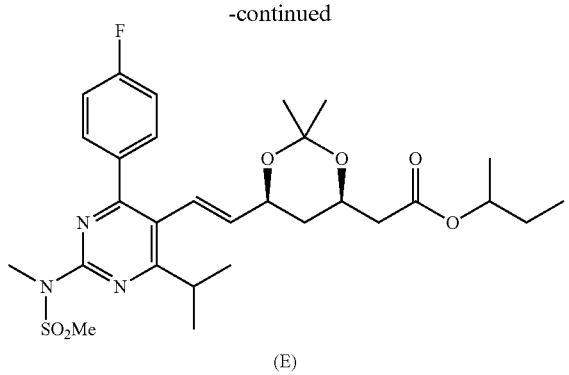

(E)

A) Procedure Using KO-tBu 2-((4R,6S)-6-((Benzo[d]thiazol-2-ylsulfonyl)methyl)-2,2-dimethyl-1,3-dioxan-4-yl)acetate sec-butyl ester (C, 8.0 g 18.1 mmol) and N-(4-(4-fluorophenyl)-5-formyl-6-isopropylpyrimidin-2-yl)-N-methylmethanesulfonamide (D, 6.4 g, 18.1 mmol) were added to 110 mL of tetrahydrofuran. The mixture was heated until complete dissolution was obtained. The solution was cooled to −50° C., followed by addition of 19.9 mL of 1 M KO-tBu in tetrahydrofuran (19.9 mmol) in 1 h. The temperature was allowed to increase to −10° C. and quenched with 100 mL of 10 w/w % of aqueous $NH_4Cl$. HPLC analysis indicated 77% product formation. The layers were separated and the organic phase washed again with 10 w/w % aqueous $NH_4Cl$. Then the reaction mixture was extracted three times with brine at a pH of 12-13 (adjusted with 4 M aqueous NaOH). After drying over $Na_2SO_4$, the organic layer was evaporated to give an oil, which slowly solidified. The solid was re-crystallized from isopropanol to give 2-((4R,6S)-6-((E)-2-(4-(4-fluorophenyl)-6-isopropyl-2-(N-methylmethanesulfonamido)pyrimidin-5-yl)vinyl)-2,2-dimethyl-1,3-dioxan-4-yl)acetate, sec-butyl ester (compound E) as a white solid (5.0 g, yield 48%). $^1$H NMR (300 MHz, $CDCl_3$) δ 7.58 (dd, 2H), 7.01 (t, 2H), 6.45 (dd, 1H), 5.40 (dd, 1H), 4.81, (m, 1H), 4.44-4.18 (m, 2H), 3.54-3.47 (m, 3H), 3.47-3.38 (m, 3H), 3.35-3.25 (m, 1H), 2.37 (ddd, 2H), 1.59-1.43 (m, 4H), 1.41 (s, 3H), 1.33 (s, 3H), 1.20, (dd, 6H), 1.14 (d, 3H), 0.83 (t, 3H).

B) Procedure Using NaO-tBu 2-((4R,6S)-6-((Benzo[d]thiazol-2-ylsulfonyl)methyl)-2,2-dimethyl-1,3-dioxan-4-yl)acetate sec-butyl ester (C, 2.0 g 4.53 mmol) and N-(4-(4-fluorophenyl)-5-formyl-6-isopropylpyrimidin-2-yl)-N-methylmethanesulfonamide (D, 1.43 g, 4.08 mmol) were added to 26 mL of tetrahydrofuran. The mixture was heated until complete dissolution was obtained. The solution was cooled to −50° C., followed by addition of 6.8 mL of 1 M NaO-tBu in tetrahydrofuran (6.8 mmol, 1.5 eq) in 1 h. The temperature was allowed to increase to −10° C. and quenched with 100 mL of 10 w/w % of aqueous $NH_4Cl$. HPLC analysis indicated 90% product formation. The product can be isolated as described in the procedure using KO-tBu.

C) Comparative Procedure Using NaHMDS

N-(4-(4-fluorophenyl)-5-formyl-6-isopropylpyrimidin-2-yl)-N-methylmethanesulfonamide (5.7 g, 16.3 mmol) and 2-((4R,6S)-6-((benzo[d]thiazol-2-ylsulfonyl)methyl)-2,2-dimethyl-1,3-dioxan-4-yl)acetate sec-butyl ester (8.0 g, 18.1 mmol) were added to 104 mL of tetrahydrofuran. The reaction mixture was heated until all the reagents were dissolved and then cooled to −70° C. At this temperature 27.2 mL of a NaHMDS solution (20% in tetrahydrofuran, total 27.2 mmol, 1.5 eq.) was added in 1 h at −70° C. When dosing was completed, the reaction mixture was stirred for 1 h at −70° C. HPLC analysis showed 68% of product formed. The reaction mixture was quenched with 100 mL of 10% aqueous $NH_4Cl$, the aqueous phase separated and the organic phase washed 2 times with 100 mL of 10% aqueous $NH_4Cl$. Next, the organic phase was washed 3 times with water at pH 12 (using 1M aqueous NaOH). The organic phase was evaporated and the residue was crystallized from isopropanol to give 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate, sec-butyl ester as a solid. $^1$H NMR (300 MHz, $CDCl_3$) δ 7.58 (dd, 2H), 7.01 (t, 2H), 6.45 (dd, 1H), 5.40 (dd, 1H), 4.81, (m, 1H), 4.44-4.18 (m, 2H), 3.54-3.47 (m, 3H), 3.47-3.38 (m, 3H), 3.35-3.25 (m, 1H), 2.37 (ddd, 2H), 1.59-1.43 (m, 4H), 1.41 (s, 3H), 1.33 (s, 3H), 1.20, (dd, 6H), 1.14 (d, 3H), 0.83 (t, 3H).

Tentative Example 3

Preparation of 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate 4-methylpentan-2-yl ester from N-(4-(4-fluorophenyl)-5-formyl-6-isopropylpyrimidin-2-yl)-N-methylmethanesulfonamide (D) and 2-((4R,6S)-6-((benzo[d]thiazol-2-ylsulfonyl)methyl)-2,2-dimethyl-1,3-dioxan-4-yl)acetate 4-methylpentan-2-yl ester The 4-methylpentan-2-yl ester of compound (5a) with $R_1$ is a radical of formula (D), $R_3$ and $R_4$ are both methyl and $R_5$ is 4-methylpentan-2-yl can be prepared according to the same procedures as outlined in Example 3 starting from 2-((4R,6S)-6-((benzo[d]thiazol-2-ylsulfonyl)methyl)-2,2-dimethyl-1,3-dioxan-4-yl)acetate 4-methylpentan-2-yl ester instead of the corresponding sec-butyl ester using the same molar amount.

For reference purposes 2-((4R,6S)-6-((E)-2-(4-(4-fluorophenyl)-6-isopropyl-2-(N-methylmethylsulfonamido)pyrimidin-5-yl)vinyl)-2,2-dimethyl-1,3-dioxan-4-yl)acetate 4-methylpentan-2-yl ester was prepared from rosuvastatin methyl ester (EP 521471). Thus, rosuvastatin methyl ester (30 g, 61 mmol) was added to 200 mL of acetonitrile and 2N aqueous NaOH was added until the pH was stable at 12.5. The reaction mixture was stirred for 2 h at 20° C. Then the pH was lowered to 5.0 with 2N aqueous HCl. To the reaction mixture was added 200 mL of ethyl acetate and the organic phase was separated and washed 2 times with 100 mL of water. The ethyl acetate phase was dried over $Na_2SO_4$, filtered and evaporated to a syrup (≈30 g of rosuvastatin acid). Part of this syrup (20 g) was dissolved in toluene and heated to reflux under azeotropic water removal for 4 h. The reaction mixture was cooled to 20° C. and stirred for 18 h. The precipitated solid was filtered, washed with toluene (2×10 mL) and dried to give 16.1 g (35 mmol) of N-(4-(4-fluorophenyl)-5-((E)-2-((2S,4R)-4-hydroxy-6-oxotetrahydro-2H-pyran-2-yl)vinyl)-6-isopropylpyrimidin-2-yl)-N-methylmethanesulfonamide as a white solid. $^1$H NMR (300 MHz, $CDCl_3$) δ 7.62 (dd, 2H), 7.11 (dd, 2H), 6.72 (dd, 1H), 5.48 (dd, 1H), 5.28-5.20 (m, 1H), 4.38-4.30 (m, 1H), 3.58 (s, 3H), 3.52 (s, 3H), 3.38-3.30 (m, 1H), 2.80-2.60 (m, 2H), 2.10-2.00 (m, 1H), 1.95-1.85 (m, 1H), 1.73-1.68 (m, 1H), 1.28 (d, 3H), 1.26 (d, 3H).

Of this compound, 2.3 g (5.0 mmol) was added to 25 mL of 2-(4-methyl)-pentanol. Then 2 drops of methanesulphonic acid were added and the reaction mixture was heated to 60° C. and stirred for 1 h. The reaction mixture was cooled to 20° C. and stirred for 18 h. Next 2,2-dimethoxypropane (0.78 g, 7.5 mol) was added and the mixture was stirred for 2 h. The reaction mixture was quenched with 20 mL of saturated aqueous NaHCO₃ followed by addition of 25 mL of ethyl acetate. The organic phase was separated and washed 2 times with 20 mL of saturated aqueous NaHCO₃ The organic phase was evaporated and the residue slowly solidified to give the title compound as a solid (2.9 g, 96% yield). $^1$H NMR (300 MHz, CDCl₃) δ 7.58 (dd, 2H), 7.01 (t, 2H), 6.46 (dd, 1H), 5.42 (dd, 1H), 4.87 (m, 1H), 4.43-4.20 (m, 2H), 3.50 (s, 3H), 3.45 (s, 3H), 3.35-3.25 (m, 1H), 2.38 (ddd, 2H), 1.59-1.43 (m, 4H), 1.40 (s, 3H), 1.35 (s, 3H), 1.20, (dd, 4H), 1.14 (d, 6H), 0.83 (t, 6H).

Example 4

Preparation of rosuvastatin-Ca (F) from-((4R,6S)-6-((E)-2-(4-(4-fluorophenyl)-6-isopropyl-2-(N-methyl-methylsulfonamido)pyrimidin-5-yl)vinyl)-2,2-dimethyl-1,3-dioxan-4-yl)acetate, sec-butyl ester (E)

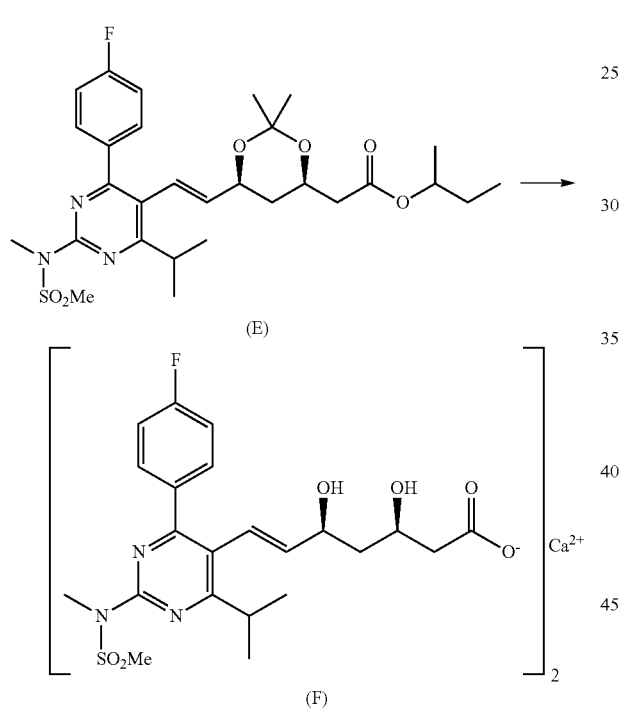

2-((4R,6S)-6-((E)-2-(4-(4-fluorophenyl)-6-isopropyl-2-(N-methylmethylsulfonamido)pyrimidin-5-yl-vinyl)-2,2-dimethyl-1,3-dioxan-4-yl)acetate, sec-butyl ester (compound E, 2.0 g, 3.46 mmol) was added to 40 mL of methanol. The mixture was heated to 35° C. until complete dissolution was obtained. The solution was cooled to 20° C. and 9 mL of 0.2 N HCl was added over a period of 2 h. The mixture was stirred for 18 h, followed by addition of 1 N NaOH in 15 min. After stirring for 1 h, 0.2 g of dicalite was added and the mixture filtered. The solution was concentrated to about 15 g, 10 mL of water was added and the mixture again concentrated to 15 g. Then 10 mL of water was added. To the obtained clear solution was added in portions over a period of 1 h, 7 mL of a solution of 4.5 w/w % Ca(OAc)₂.H₂O (1.2 equiv.) in water. Upon addition white precipitate was formed. After 1 h the precipitate was filtered and dried to give 1.34 g (2.68 mmol) of the calcium salt of rosuvastatin as a slightly yellow solid (yield 77%). $^1$H NMR (300 MHz, DMSO) δ 7.72 (dd, 2H), 7.29 (t, 2H), 6.51 (d, 1H), 5.54 (dd, 1H), 4.21 (dd, 1H), 3.71 (m, 1H), 3.55 (s, 3H), 3.51-3.41 (m, 4H), 2.09 (dd, 1H), 1.92 (dd, 1H), 1.57-1.42 (m, 1H), 1.36-1.25 (m, 1H), 1.22 (dd, 6H).

The invention claimed is:

1. A process for the preparation of a compound of general formula R₁—C≡C—R₂ or salt thereof, wherein R₁ is a radical chosen from the group consisting of the radicals of formula (A), (B), (C) and (D):

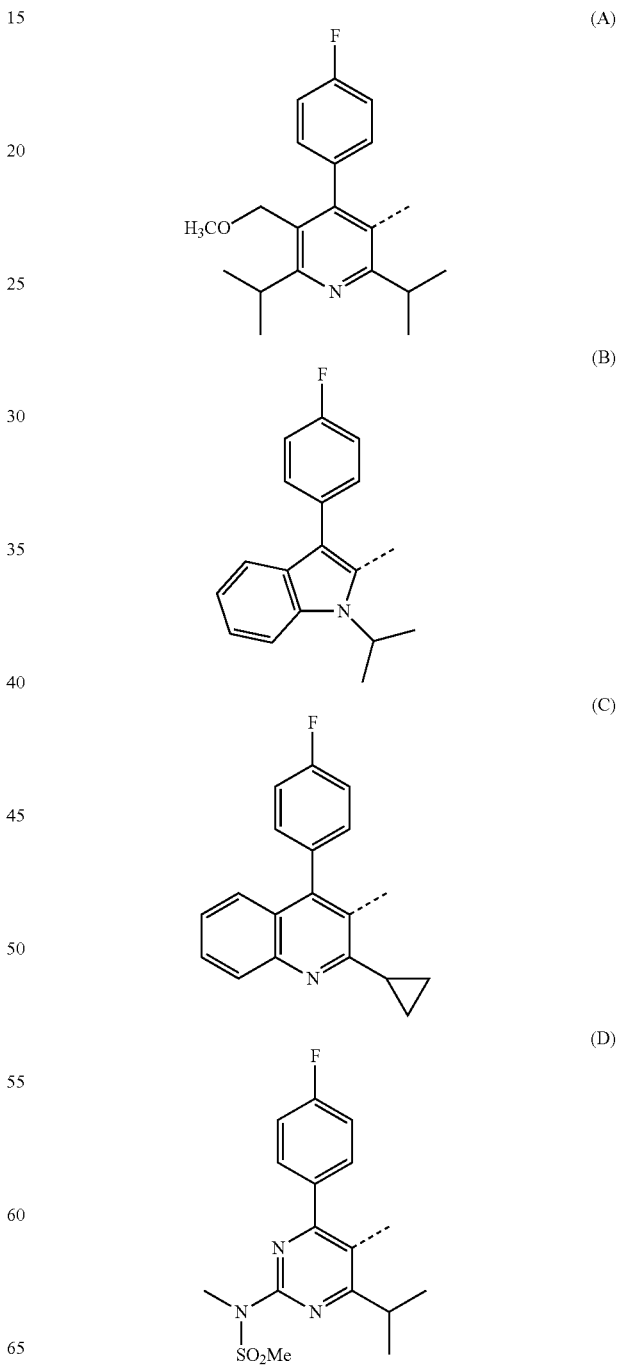

and wherein $R_2$ is a radical of general formula (E) or (F):

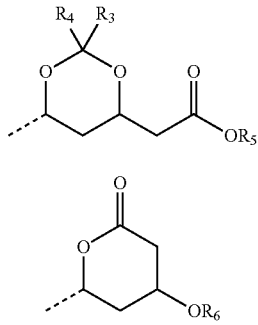

wherein $R_3$ and $R_4$ each independently stand for an alkyl with 1 to 12 carbon atoms, or an alkenyl with 1 to 12 carbon atoms, or a cycloalkyl with 3 to 7 carbon atoms, or a cycloalkenyl with 3 to 7 carbon atoms, or an aryl with 6 to 10 carbon atoms, or an aralkyl with 7 to 12 carbon atoms, or wherein $R_3$ and $R_4$ form a ring together with the carbon atom to which they are bound, wherein $R_5$ is an alkyl or alkenyl group with 1 to 4 four carbon atoms, and wherein $R_6$ is an alcohol protecting group, the process comprising reacting a compound of formula $R_1$—CH=O with a compound of formula $R_2$—$CH_2$—$SO_2$—$R_7$ wherein $R_1$ and $R_2$ are as defined above and $R_7$ is a radical of general formula $R_{7'}$ or $R_{7''}$:

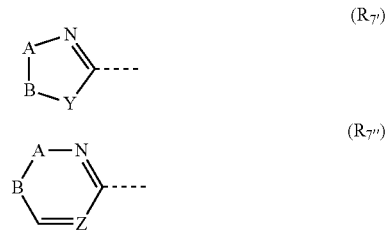

wherein A-B is C=C or N=N, or wherein A-B is part of a aromatic five- or six-membered ring, optionally substituted, wherein Y is sulfur or alkyl-substituted nitrogen, and wherein Z is nitrogen or CH, in the presence of an alkaline metal alkoxy base with a pKa value of from 16 to 21.

2. The process according to claim 1, wherein the alkaline metal alkoxy base is chosen from the group consisting of lithium tert-butoxide, lithium ethoxide, lithium methoxide, potassium tert-butoxide, potassium ethoxide, potassium methoxide, sodium tert-butoxide, sodium ethoxide and sodium methoxide.

3. The process according to claim 1, wherein $R_3$ is ethyl or methyl and $R_4$ is ethyl or methyl or $R_3$ and $R_4$ form a cyclopentyl ring or a cyclohexyl ring together with the carbon atom to which they are bound, $R_5$ is sec-butyl, tert-butyl, ethyl, methyl, or iso-propyl, $R_6$ is methoxyethoxymethyl, tetrahydrofuranyl or tetrahydropyranyl and $R_7$ is 1-methyl-1H-tetrazol-5-yl, 1-phenyl-1H-tetrazol-5-yl, 1-tert-butyl-1-H-tetrazol-5-yl or benzothiazol-2-yl.

4. The process according to claim 1, wherein $R_1$ is a radical of the formula (D).

5. The process according to claim 1, which further comprises a subsequent step of deprotection and isolation of the compound of general formula $R_1$—C=C—$R_2$ or a salt thereof to yield a compound of the general formula $R_1$—C=C—$R_2'$ or a salt thereof, wherein $R_1$ is as defined above and $R_2'$ is a radical of general formula (G):

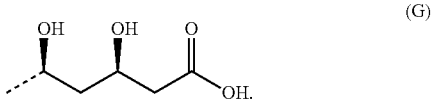

6. The process according to claim 5, wherein said compound of the general formula $R_1$—C=C—$R_2'$ or a salt thereof obtained after deprotection and isolation is rosuvastatin or a calcium salt of rosuvastatin.

* * * * *